US008666499B2

(12) United States Patent
Youn et al.

(10) Patent No.: US 8,666,499 B2
(45) Date of Patent: Mar. 4, 2014

(54) ARTIFICIAL NERVE NETWORKING SYSTEM AND METHOD FOR FUNCTIONAL RECOVERY OF DAMAGED NERVE

(75) Inventors: In Chan Youn, Seoul (KR); Kui Won Choi, Seoul (KR); Jun Kyo Suh, Seoul (KR); Ji Yoon Kang, Seoul (KR); Jin Seok Kim, Seoul (KR); Jun Uk Chu, Seoul (KR); Ick Chan Kwon, Seoul (KR); Kwang Meyung Kim, Seoul (KR)

(73) Assignee: Korean Institute of Science and Technology, Hawolgok-Dong Seongbuk-Gu Seoul (KR)

( * ) Notice: Subject to any disclaimer, the term of this patent is extended or adjusted under 35 U.S.C. 154(b) by 105 days.

(21) Appl. No.: 13/166,250

(22) Filed: Jun. 22, 2011

(65) Prior Publication Data
US 2012/0253423 A1    Oct. 4, 2012

(30) Foreign Application Priority Data
Mar. 29, 2011    (KR) .................. 10-2011-0027964

(51) Int. Cl.
*A61N 1/00*    (2006.01)
(52) U.S. Cl.
USPC ............... 607/50; 607/59; 607/60; 607/61; 607/115; 607/116; 607/118

(58) Field of Classification Search
USPC ............... 607/1–2, 50, 59–61, 115–116, 118
See application file for complete search history.

(56) References Cited

U.S. PATENT DOCUMENTS

| | | | |
|---|---|---|---|
| 2006/0095105 A1* | 5/2006 | Jog et al. ...................... 607/116 |
| 2007/0055324 A1* | 3/2007 | Thompson et al. ............ 607/60 |
| 2008/0161867 A1 | 7/2008 | Zdravkovic |
| 2008/0228240 A1 | 9/2008 | Edell et al. |
| 2010/0152811 A1 | 6/2010 | Flaherty |

* cited by examiner

*Primary Examiner* — Deborah Malamud
(74) *Attorney, Agent, or Firm* — GableGotwals (57) ABSTRACT

Disclosed are a system and a method for artificial nerve networking capable of restoring a damaged nerve and allowing selective detection, analysis, transmission and stimulation of a signal from the damaged nerve. The artificial nerve networking system according to an embodiment of the present disclosure includes: a first nerve conduit connected at one end of a damaged nerve; a second nerve conduit connected at the other end of the damaged nerve; and an artificial nerve networking unit electrically connected to the first nerve conduit and the second nerve conduit and recovering the function of the damaged nerve by transmitting and receiving a signal to and from the damaged nerve.

5 Claims, 7 Drawing Sheets

ARTIFICIAL NERVE NETWORKING SYSTEM AND METHOD FOR FUNCTIONAL RECOVERY OF DAMAGED NERVE

CROSS-REFERENCE TO RELATED APPLICATIONS

This application claims priority under 35 U.S.C. §119 to Korean Patent Application No. 10-2011-0027964, filed on Mar. 29, 2011, in the Korean Intellectual Property Office, the disclosure of which is incorporated herein by reference in its entirety.

TECHNICAL FIELD

The present disclosure relates to a system and a method for functional recovery of a damaged nerve.

BACKGROUND

When nerves are severed or damaged otherwise, stimulations inside and outside the organism may not be properly transmitted. This may be very hazardous to the organism. Especially, spinal nerves are known as one of the most difficult-to-regenerate human tissues. Once the spinal nerves are damaged, the function of the motor and sensory nerves may be permanently lost. Damage to the spinal nerve causes severe pain in addition to the loss of motor function, as well as many complications such as cystitis, bedsore, autonomic hyperreflexia, muscle spasm, heterotopic ossification, etc., leaving patients in pain in their lifetime.

For functional recovery of the damaged nerve, various therapies including cell therapy, tissue engineering-based therapy, rehabilitation therapy, drug therapy, nerve stimulation-based therapy, etc. are studied, but they have the following limitations.

Cell therapy involves introduction of bone marrow-derived stem cells to the damaged nerve to induce regeneration of the nerve tissue. However, it is still difficult to remain the cavity in the spinal cord, and the introduced stem cells exhibit low viability.

Tissue engineering-based therapy employs a tissue engineering support or stem cells to induce regeneration of the nerve tissue. However, this method is effective only for the peripheral nerves which have excellent regenerating ability, and its application is restricted.

As for drug and rehabilitation therapies, there is no drug available for the functional recovery of the spinal nerve, and the rehabilitation therapy is only a supplementary measure to improve conditions.

Treatment using an apparatus for stimulating nerves is based on electrical stimulation using implantable electrical/electronic devices and software for controlling them, without drug administration. However, the existing nerve-stimulating apparatus allows only the recovery of cerebral function as well as the relieving of pain.

Accordingly, they are restricted in recovering the function of damaged nerves by regenerating them.

SUMMARY

The present disclosure is directed to providing a system and a method for artificial nerve networking, capable of recovering a damaged nerve and selectively detecting, analyzing, transmitting and stimulating from the signal from the damaged nerve.

An artificial nerve networking system according to an embodiment of the present disclosure includes: a first nerve conduit connected at one end of a damaged nerve; a second nerve conduit connected at the other end of the damaged nerve; and an artificial nerve networking unit electrically connected to the first nerve conduit and the second nerve conduit and recovering the function of the damaged nerve by transmitting and receiving a signal to and from the damaged nerve.

The first nerve conduit and the second nerve conduit may each include: a support connected at an end of the damaged nerve; a cavity-type channel formed in the body of the support; an electrode layer formed along the inner wall of the channel; and an external electrode electrically connected to the electrode layer. Nerve cells may grow along the channel at the end of the damaged nerve, and the grown nerve cells may be electrically connected to the electrode layer.

The support may have plurality of channels.

The artificial nerve networking unit may include: a first implantable module implanted in an organism and electrically connected to the first nerve conduit; a second implantable module implanted in the organism and electrically connected to the second nerve conduit; and an external module provided outside the organism. A nerve signal may be transmitted among the first implantable module, the second implantable module and the external module via wireless communication.

The first implantable module and the second implantable module may each include: an amplifier amplifying the signal from the damaged nerve received through the first nerve conduit and the second nerve conduit; an analog-to-digital (AD) converter converting the signal amplified by the amplifier to a digital signal; a digital signal processor receiving and analyzing the digital signal converted by the AD converter and transmitting the digital signal to one of the first implantable module, the second implantable module and the external module via wireless communication, or receiving and analyzing a digital signal received from one of the first implantable module, the second implantable module and the external module and transmitting it to the nerve cells grown along the channel; a digital-to-analog (DA) converter converting the digital signal received from the digital signal processor into an analog signal; a stimulator transmitting an electrical stimulation signal to the nerve cells grown along the plurality of channels using the analog signal converted by the DA converter; and a multiplexer electrically matching the nerve cells grown along the plurality of channels with the amplifier and the stimulator according to the command from the digital signal processor.

The digital signal processor may employ a multilayer perceptron algorithm.

The first implantable module and the second implantable module may each further comprise: an internal communication unit for transmitting and receiving a signal to and from the external module via wireless communication; and a power receiver wirelessly receiving power from the external module.

The external module may comprise: an external communication unit for transmitting and receiving a signal to and from the internal communication unit; a power supply wirelessly supplying power to the power receiver; and an external controller analyzing the nerve signal received from the external communication unit and determining a parameter of the multilayer perceptron algorithm according to the analysis result.

An artificial nerve networking method according to an embodiment of the present disclosure comprises: regenerating nerve cells near a proximal end of the damaged nerve using a first nerve conduit; regenerating nerve cells near a distal end of the damaged nerve using a second nerve conduit; detecting an efferent nerve signal using a first implantable module implanted in an organism and electrically connected to the first nerve conduit; detecting an afferent nerve signal using a second implantable module implanted in the organism and electrically connected to the second nerve conduit; transmitting the efferent nerve signal detected by the first implantable module to the second implantable module via wireless communication; and transmitting the afferent nerve signal detected by the second implantable module to the first implantable module via wireless communication.

An artificial nerve networking method according to an embodiment of the present disclosure may further comprise: transmitting an afferent electrical stimulation signal to the nerve cells at the proximal end of the damaged nerve according to the received afferent nerve signal, by the first implantable module; and transmitting an efferent electrical stimulation signal to the nerve cells at the distal end of the damaged nerve according to the received efferent nerve signal, by the second implantable module.

In an artificial nerve networking method according to an embodiment of the present disclosure, the first nerve conduit and the second nerve conduit each may comprise a porous polymer electrode, and the porous polymer electrode may be used to selectively detect the efferent nerve signal or the afferent nerve signal and selectively transmit an electrical stimulation signal to the nerve cells at the proximal end of the damaged nerve or to the nerve cells at the distal end of the damaged nerve.

The selective detection of the efferent nerve signal or the afferent nerve signal and the selective transmission of the electrical stimulation signal to the nerve cells at the proximal end of the damaged nerve or to the nerve cells at the distal end of the damaged nerve may be performed using a multilayer perceptron algorithm.

An artificial nerve networking method according to an embodiment of the present disclosure may further comprise: wirelessly supplying power to the first implantable module and the second implantable module and receiving and analyzing the efferent nerve signal or the afferent nerve signal from the first implantable module and the second implantable module via wireless communication, by an external module external module provided outside the organism; and determining a parameter of the multilayer perceptron algorithm according to the analysis result, by the external module.

Other features and aspects will be apparent from the following detailed description, the drawings, and the claims.

BRIEF DESCRIPTION OF THE DRAWINGS

The above and other objects, features and advantages of the present disclosure will become apparent from the following description of certain exemplary embodiments given in conjunction with the accompanying drawings, in which.

It should be understood that the appended drawings are not necessarily to scale, presenting a somewhat simplified representation of various preferred features illustrative of the basic principles of the disclosure. The specific design features of the disclosure as disclosed herein, including, for example, specific dimensions, orientations, locations and shapes, will be determined in part by the particular intended application and use environment.

In the figures, reference numerals refer to the same or equivalent parts of the disclosure throughout the several figures of the drawings.

DETAILED DESCRIPTION OF EMBODIMENTS

The advantages, features and aspects of the present disclosure will become apparent from the following description of the embodiments with reference to the accompanying drawings, which is set forth hereinafter. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. The terminology used herein is for the purpose of describing particular embodiments only and is not intended to be limiting of the example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail with reference to the accompanying drawings.

Figure 1:
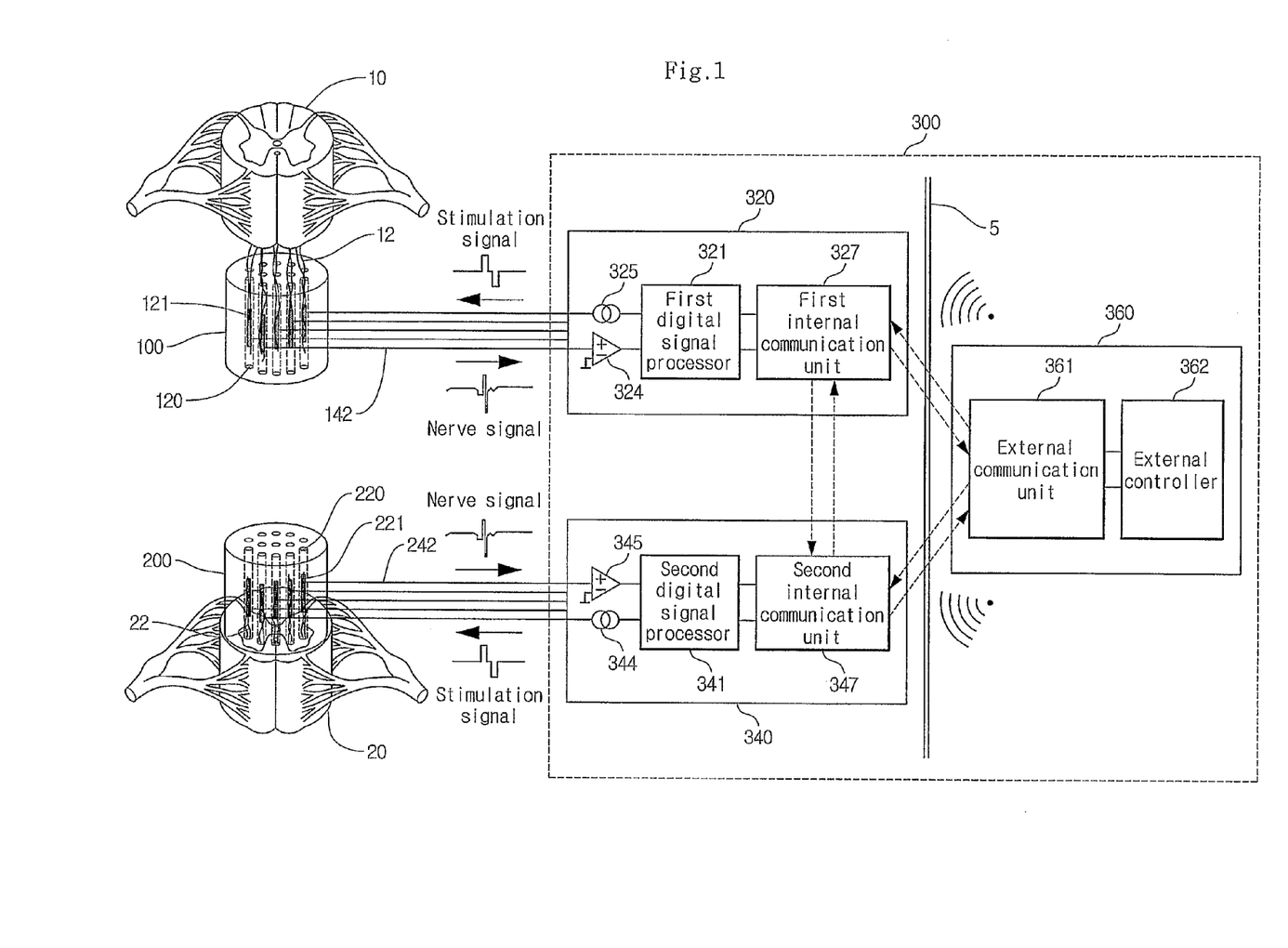
FIG. 1 illustrates an operation of an artificial nerve networking system according to an embodiment of the present disclosure disposed between spinal nerves and transmitting and receiving a nerve signal.

FIG. 1 illustrates an operation of an artificial nerve networking system according to an embodiment of the present disclosure disposed between spinal nerves and transmitting and receiving a nerve signal.

Referring to FIG. 1, an artificial nerve networking system according to an embodiment of the present disclosure comprises a first nerve conduit 100, a second nerve conduit 200, and an artificial nerve networking unit 300.

The first nerve conduit 100 is electrically connected to a proximal spinal cord stump 10, and detects a nerve signal or transmits an electrical stimulation signal. Specifically, the first nerve conduit 100 has a plurality of cavity-type channels 120, and an electrode layer 121 is formed in the channel 120. The electrode layer 121 is electrically connected to an efferent axon 12 regenerated at the end of the proximal spinal cord stump 10.

Especially, the first nerve conduit 100 has the plurality of channels 120, such that the efferent axon 12 of each of a plurality of regenerated nerve cells is connected to a first implantable module 320, which will be described later, via a second conductor 142 comprising, e.g., a wire so as to transmit an efferent nerve signal.

The second nerve conduit 200 is electrically connected to a distal spinal cord stump 20, and detects a nerve signal or transmits an electrical stimulation signal. Specifically, the second nerve conduit 200 has a plurality of cavity-type channels 220, and an electrode layer 221 is formed in the channel 220. The electrode layer 221 is electrically connected to an afferent axon 22 regenerated at the end of the distal spinal cord stump 20.

Likewise, the second nerve conduit 200 has the plurality of channels 220, such that the afferent axon 22 of each of a plurality of regenerated nerve cells is connected to a second implantable module 340, which will be described later, via a second conductor 242 comprising, e.g., a wire so as to transmit an afferent nerve signal.

Details about the configuration and operation of the first nerve conduit 100 and the second nerve conduit 200, which each comprises a porous polymer electrode capable of selectively detecting a nerve signal from each of the plurality of nerve cells, will be described later referring to FIGS. 3 through 5.

The artificial nerve networking unit 300 comprises a first implantable module 320, a second implantable module 340, and an external module 360. The artificial nerve networking unit 300 is electrically connected to the first nerve conduit 100 and the second nerve conduit 200 so as to allow transmission of a nerve signal to and from a damaged and severed nerve.

The first implantable module 320 is implanted in an organism, i.e. a human or an animal, and is electrically connected to the first nerve conduit 100. Referring to FIG. 1, the first implantable module 320 is implanted in a skin 5. It comprises a first digital signal processor 321, a first amplifier 324, a first stimulator 325, and a first internal communication unit 327.

The first amplifier 324 receives the efferent nerve signal from the first nerve conduit 100 and amplifies it. The first digital signal processor 321 analyzes the amplified efferent nerve signal and transmits the result to the second implantable module 340 or the external module 360 via the first internal communication unit 327. And, the first stimulator 325 transmits the electrical stimulation signal to the first nerve conduit 100 according to the command from the digital signal processor 321.

The second implantable module 340 is also implanted in the skin 5. It comprises a second digital signal processor 341, a second amplifier 344, a second stimulator 345, and a second internal communication unit 347.

The external module 360 is provided outside the organism. It comprises an external communication unit 361, and an external controller 362. Referring to FIG. 1, the external module 360 is provided outside the skin 5, and transmits and receives a nerve signal to and from the first implantable module 320 and the second implantable module 340 via the external communication unit 361. The external controller 362 analyzes the nerve signal monitored via the external communication unit 361 and determines a parameter of an artificial nerve networking algorithm, i.e. a multilayer perceptron algorithm, which will be described later.

An operation of the artificial nerve networking system according to an embodiment of the present disclosure will be described roughly. First, the efferent axon 12 of the proximal spinal cord stump 10 grows along the channel 120 and is connected to the electrode layer 121. The electrode layer 121 is connected to the first implantable module 320 via the second conductor 142, and the efferent nerve signal is transmitted to and amplified by the first amplifier 324. The amplified signal is transmitted by the first digital signal processor 321 to the second internal communication unit 347 or to the external communication unit 361 via the first internal communication unit 327.

The second internal communication unit 347 receives the efferent nerve signal and transmits it to the second digital signal processor 341. The second digital signal processor 341 analyzes the efferent nerve signal and transmits the electrical stimulation signal to the second nerve conduit 200 via the second stimulator 345.

In the same manner, the afferent axon 22 of the distal spinal cord stump 20 grows along the channel 220 and is connected to the electrode layer 221. The electrode layer 221 is connected to the second implantable module 340 via the second conductor 242, and the afferent nerve signal is transmitted to and amplified by the second amplifier 344. The amplified signal is transmitted by the second digital signal processor 341 to the first internal communication unit 327 or to the external communication unit 361 via the second internal communication unit 347.

The first implantable module 320 receives the afferent nerve signal and transmits the electrical stimulation signal to the first nerve conduit 100 via the first internal communication unit 327, the first digital signal processor 321 and the first stimulator 325.

The external communication unit 361 detects and monitors the afferent or efferent nerve signal from the first internal communication unit 327 and the second internal communication unit 347, determines a parameter of a multilayer perceptron algorithm so as to set the channels 120, 220 of the nerve conduits 100, 200 appropriately for the plurality of nerve signals, and transmits the parameter to the first digital signal processor 321 and the second digital signal processor 341 of the first implantable module 320 and the second implantable module 340 via the external communication unit 361.

Figure 2:
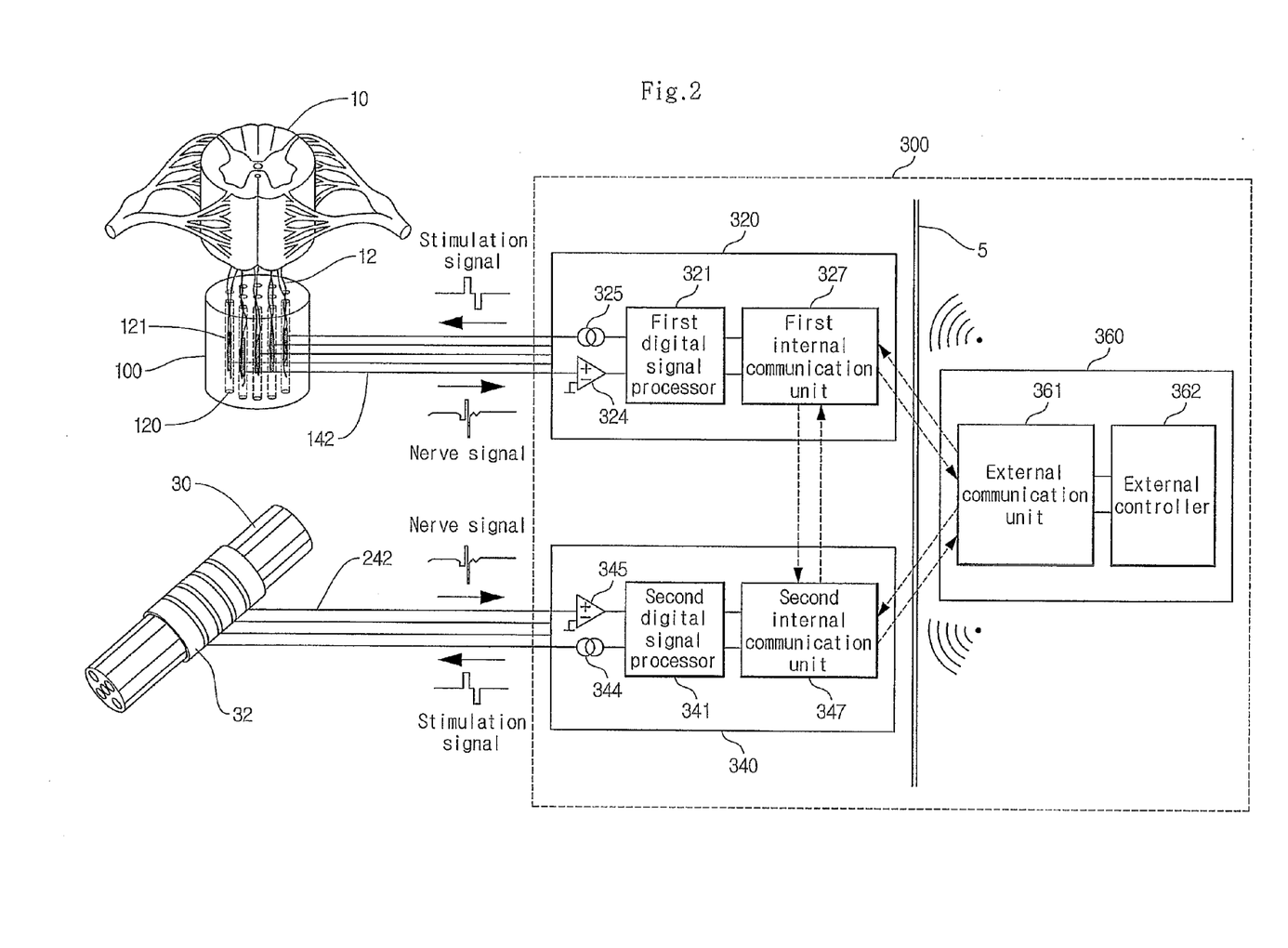
FIG. 2 illustrates an operation of an artificial nerve networking system according to an embodiment of the present disclosure disposed between spinal nerves and peripheral nerves and transmitting and receiving a nerve signal.

FIG. 2 illustrates an operation of an artificial nerve networking system according to an embodiment of the present disclosure disposed between spinal nerves and peripheral nerves and transmitting and receiving a nerve signal.

Whereas the first nerve conduit 100 is connected to the proximal spinal cord stump 10 and the second nerve conduit 200 is connected to the distal spinal cord stump 20 in FIG. 1, the first nerve conduit 100 is connected to the proximal spinal cord stump 10 and the second nerve conduit 200 is directly connected to a peripheral nerve 30 in FIG. 2.

Referring to FIG. 2, a cuff electrode 32 is disposed at the peripheral nerve 30, and the cuff electrode 32 is connected to the second implantable module 340 via the second conductor 242. As such, by directly connecting the first nerve conduit 100 to the peripheral nerve 30, it is possible to allow transmission and reception of a nerve signal between the damaged proximal spinal cord stump 10 and the peripheral nerve 30 where disorder occurs due to the nerve damage, thus allowing selective treatment of the particular site of disorder.

Except for the connection, details about the operation are the same as that of FIG. 1 and thus will be omitted. Hereinafter, the nerve conduit used in the present disclosure will be described in detail referring to FIGS. 3 through 5.

Figure 3:
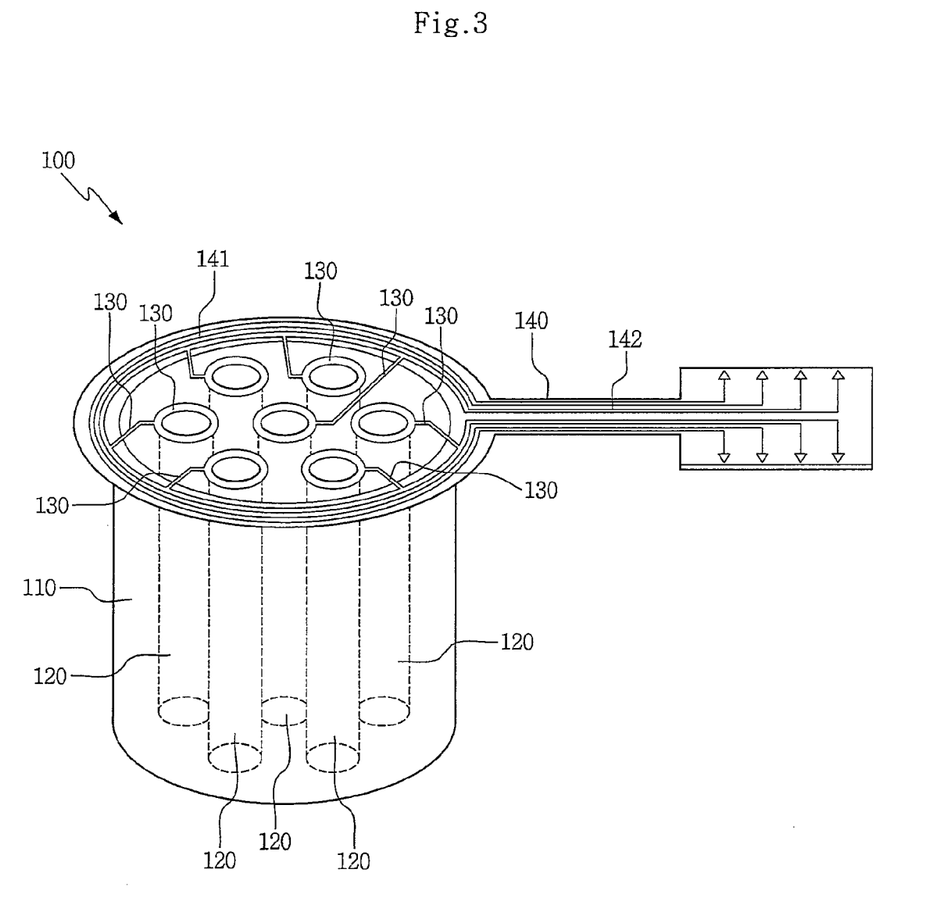
FIG. 3 is a perspective view of a nerve conduit used in an artificial nerve networking system according to an embodiment of the present disclosure.

FIG. 3 is a perspective view of a nerve conduit used in an artificial nerve networking system according to an embodiment of the present disclosure. For convenience's sake, description will be made only about the first nerve conduit 100.

Referring to FIG. 3, the first nerve conduit 100 comprises a cylindrical support 110, and the plurality of cavity-type channels 120 formed in the body of the support 110. As will be described later, each channel 120 has the electrode layer 121 formed along the inner wall thereof (see FIGS. 4 and 5).

The support 110 has a cylindrical body, and is cut to be connected to the end of the damaged nerve. The support 110 is made of polyurethane and consists of a plurality of fibers. However, the material of the support 110 is not limited to polyurethane, and any biocompatible material that can be processed into a desired shape with an adequate rigidity may be used for the support 110.

The plurality of channels 120 are formed in the body of the support 110 along a longitudinal direction of the support 110. For convenience of illustration, the channels 120 are depicted by broken lines.

An external electrode 130 is formed at the inlet (i.e., the upside surface of the support 110) of each of the plurality of channels 120. As will be described later, the external electrode 130 is electrically connected to the electrode layer 121, and is also electrically connected to a contact electrode 140 formed at the upside surface of the support 110.

The contact electrode 140 comprises a ring-shaped first conductor 141 formed along the upside circumference of the support 110, and the second conductor 142 electrically connected to the first conductor 141.

As shown in FIG. 3, the first conductor 141 is electrically connected to the external electrodes 130 which are connected to the channels 120, and the second conductor 142 is electrically connected to the first implantable module 320.

Figure 4:
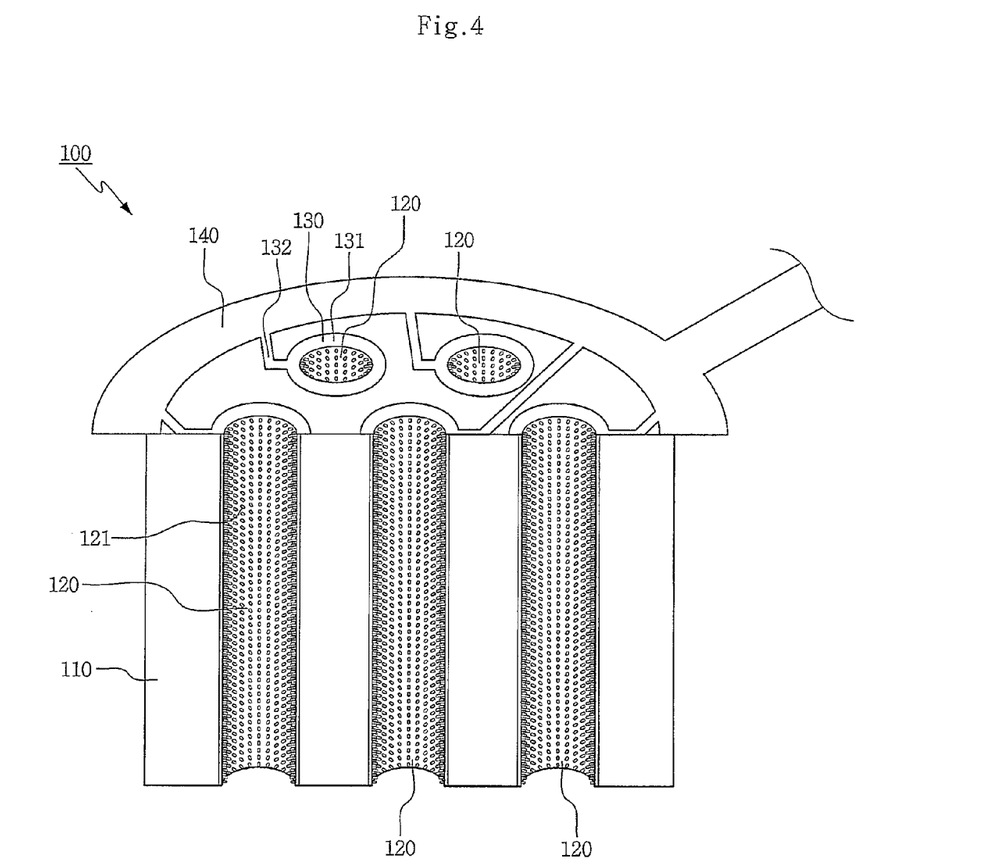
FIG. 4 is a cross-sectional perspective view of the nerve conduit shown in FIG. 3.

FIG. 4 is a cross-sectional perspective view of the nerve conduit shown in FIG. 3. In FIG. 4, the first nerve conduit 100 is shown cut in half along its longitudinal direction.

As seen from FIG. 4, the electrode layer 121 is formed along the inner wall of the channel 120. According to this embodiment, the electrode layer 121 comprises a plurality of nanofibers extending along the channel 120.

It should be understood that the diameter of the nanofiber and the distance between the nanofibers are exaggerated in FIG. 4 for the convenience of illustration. The nanofiber may be finer and denser depending on situations.

For example, the nanofiber may comprise GZnO, i.e. gallium (Ga)-doped zinc oxide (ZnO), whose electrical properties are controllable. Being a ceramic material, GZnO has excellent conductivity and exhibits minimized toxicity when used as an electrode, unlike other metals, thus providing superior biocompatibility.

In order to uniformly distribute the nanofiber on the inner wall of the channel 120 and to utilize the distributed nanofiber layer as the electrode layer 121, the so-called sol-gel process is employed in this embodiment. By employing the sol-gel process, the nanofiber can be grown uniformly on the inner wall of the cavity-type channel 120, and an electrical network of the nanofibers can be formed, so that the inside the channel 120 may be electrically conducting by the nanofibers.

Details about the sol-gel process will not be described here since they are well known to those skilled in the art.

The external electrode 130 is formed at the inlet of each of the channels 120, and is electrically connected to the electrode layer 121. The external electrode 130 comprises a ring-shaped first electrode 131 formed along the circumference of the inlet of the channel 120, and a second electrode 132 electrically connected to the first electrode 131.

The first electrode 131 is connected to a portion of the electrode layer 121, which is exposed on the upside surface of the support 110, and thus is electrically connected to the electrode layer 121. The second electrode 132 is electrically connected to the first conductor 141 of the contact electrode 140.

The configuration of the external electrode 130 electrically connected to each of the electrode layers 121 formed in the channel 120 is identical.

Now, the configuration of the channel 120 will be described in detail referring to FIG. 5.

Figure 5:
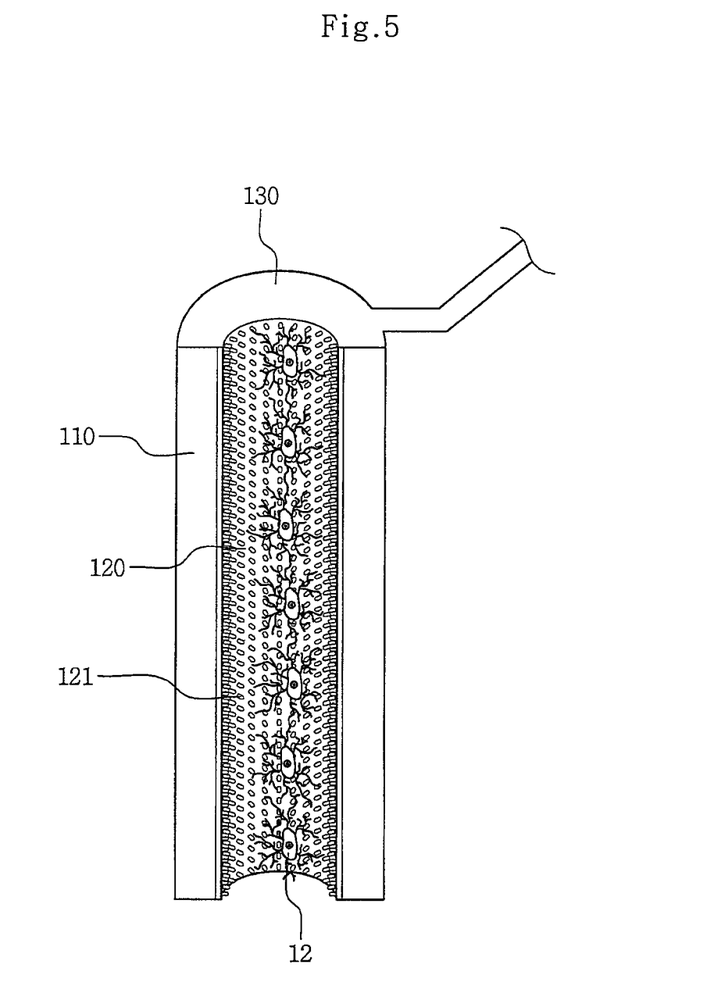
FIG. 5 is a cross-sectional view showing a part of the nerve conduit shown in FIG. 4.

FIG. 5 is a cross-sectional view showing a part of the nerve conduit shown in FIG. 4. The configuration of one channel 120 is shown in FIG. 5. The other channels have the same configuration.

As seen from FIG. 5, nerve cells, i.e. efferent axons 12, grow from the end of the severed nerve inside the channel 120. Although only one strand of the efferent axons 12 is shown in FIG. 5, multiple strands of nerve cells may grow (regenerate) in the channel 120. Details about the method of regenerating the nerve cells will not be described here since they are well known in the art.

When the efferent axon 12 grows in the channel 120, it grows along the inner wall of the channel 120 using the nanofiber as support. As the efferent axon 12 grows using the nanofiber as support, the efferent axon 12 is rigidly fixed inside the channel 120.

As described above, since the nanofibers form the electrode layer 121 on the inner wall of the channel 120, the efferent axon 12 is naturally electrically connected to the electrode layer 121.

Accordingly, the efferent nerve signal transmitted from the efferent axon 12 to the electrode layer 121 may be detected by the external electrode 130 and transmitted to outside via the contact electrode 140. Also, an external electrical signal transmitted through the contact electrode 140 may be transmitted to the efferent axon 12 via the external electrode 130 and the electrode layer 121.

Although a plurality of channels 120 are formed in the support 110 at the same time in this embodiment, only one channel 120 may be formed in the support 110. But, since the nerve comprises bundles of nerve cells, and each nerve cell bundle is often connected to a different organ, by forming a plurality of channels 120 in the support 110 and selectively growing the nerve cell bundles in the respective channels 120, it may be much easier to classify and transmit the nerve signals.

The support 110 with the plurality of channels 120 may be formed by perforating the plurality of channels 120 in one cylindrical support 110 by microetching. Alternatively, individual nerve conduits having one channel 120 may be tied together.

In the present disclosure, wireless communication and artificial nerve networking are employed in order to selectively detect, analyze and transmit nerve signals using the nerve conduits 100, 200. Hereinafter, the configuration and operation of the artificial nerve networking unit 300 according to the present disclosure will be described in detail referring to FIGS. 6 and 7.

Figure 6:
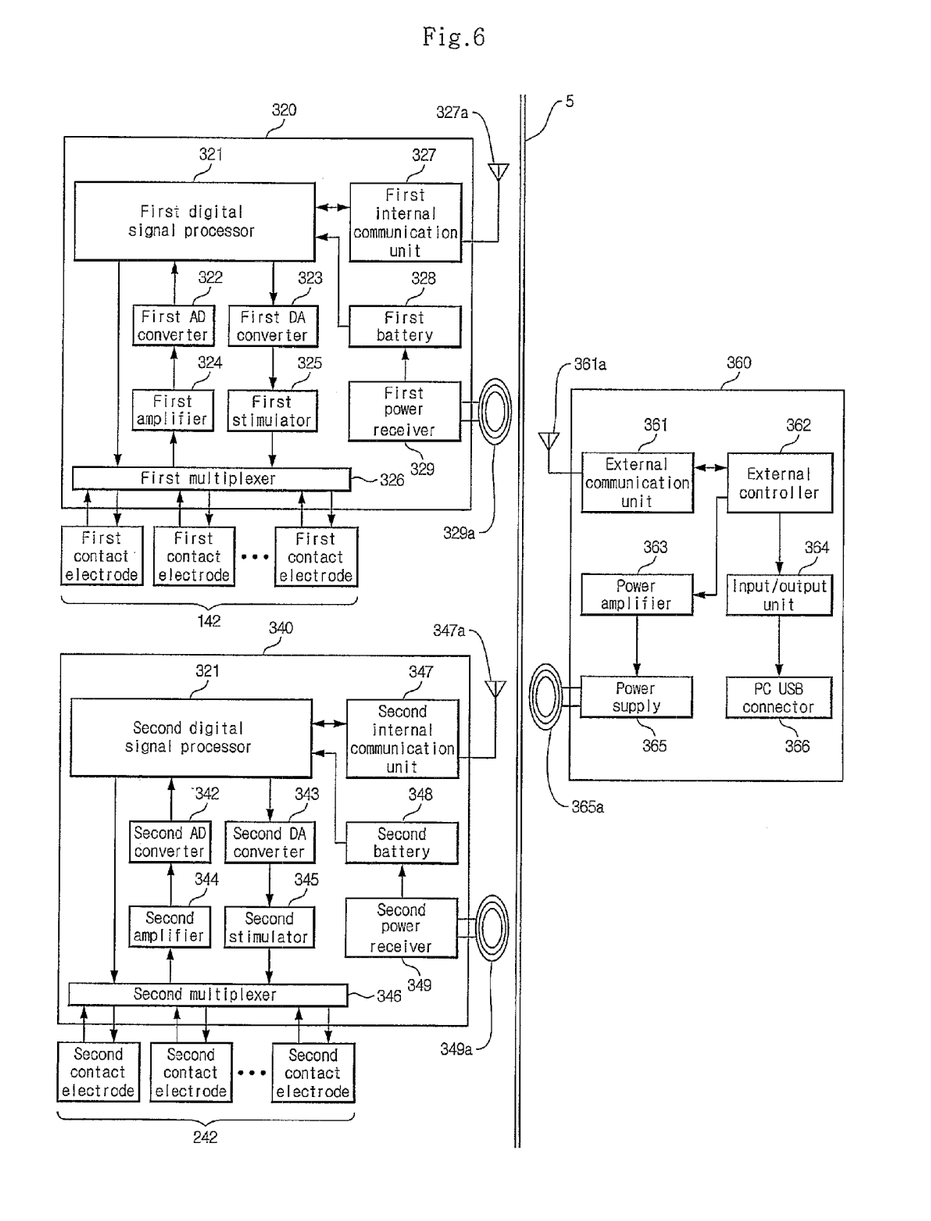
FIG. 6 shows a detailed configuration of an artificial nerve networking unit used in an artificial nerve networking system according to an embodiment of the present disclosure.

FIG. 6 shows a detailed configuration of the artificial nerve networking unit used in the artificial nerve networking system according to an embodiment of the present disclosure.

Referring to FIG. 6, the artificial nerve networking unit 300 comprises a first implantable module 320, a second implantable module 340, and an external module 360.

The first implantable module 320 comprises the first digital signal processor 321, a first analog-to-digital (AD) converter 322, a first digital-to-analog (DA) converter 323, the first amplifier 324, the first stimulator 325, a first multiplexer 326, the first internal communication unit 327, a first battery 328, and a first power receiver 329.

Details about the function of the first digital signal processor 321, the first amplifier 324 and the first stimulator 325 will be omitted since they were described referring to FIG. 1.

The first multiplexer 326 selectively matches the nerve signals received from a plurality of 'first contact electrodes', i.e. the second conductor 142, with a limited number of the first amplifier 324 and the first stimulator 325. The matching operation by the first multiplexer 326 is performed according to the command from the first digital signal processor 321. The first digital signal processor 321 performs the operation using the multilayer perceptron algorithm. Details will be described later referring to FIG. 7.

The first AD converter 322 converts the analog efferent nerve signal amplified by the first amplifier 324 to a digital signal, so that the first digital signal processor 321 may analyze it.

Conversely, the first DA converter 323 converts the digital signal transmitted from the first digital signal processor 321 to an analog signal.

As described referring to FIG. 1, the first internal communication unit 327 transmits and receives the nerve signal to and from the second implantable module 340 or the external module 360. As shown in FIG. 6, the first internal communication unit 327 may comprise a radio frequency (RF) antenna 327a.

The first power receiver 329 receives power wirelessly from the external module 360 and supplies it to the first battery 328. The first battery 328 is charged by the supplied power and supplies power to the first digital signal processor 321, etc.

As shown in FIG. 6, the first power receiver 329 may comprise a power coil 329a for receiving the power. The power coil 329a of the first power receiver 329 receives power via wireless communication from a power coil 365a of a power supply 365 of the external module 360, which will be described later. Details about the wireless power transmission based on electromagnetic induction will not be described since it is well known to those skilled in the art.

The external module 360 comprises an external communication unit 361, an external controller 362, a power amplifier 363, an input/output unit 364, a power supply 365, and a PC USB connector 366.

The external communication unit 361 transmits and receives the nerve signal via wireless communication to and from the first internal communication unit 327 of the first implantable module 320 and the second internal communication unit 347 of the second implantable module 340. As shown in FIG. 6, the external communication unit 361 may comprise an RF antenna 361a.

The external controller 362 analyzes the nerve signal monitored through the external communication unit 361 and determines the parameter of the artificial nerve networking algorithm, i.e. the multilayer perceptron algorithm, as will be described later.

The power amplifier 363 amplifies the power supplied to the external module 360 and supplies the amplified power to the power supply 365. The power supply 365 supplies the power transmitted from the power amplifier 363 wirelessly to the first power receiver 329 and a second power receiver 349 via the power coil 365a.

The input/output unit 364 is a module for providing a user interface for control of the external module 360. It may comprise a monitor, a keyboard, or the like.

The PC USB connector 366 may be equipped at the external module 360 to drive the external module 360 in association with an external PC.

The second implantable module 340 comprises the second digital signal processor 341, a second AD converter 342, a second DA converter 343, the second amplifier 344, the second stimulator 345, a second multiplexer 346, second internal communication unit 347, a second battery 348, and the second power receiver 349.

A detailed description about the configuration and operation of the second implantable module 340 will be omitted since they are similar to those of the first implantable module 320.

Figure 7:
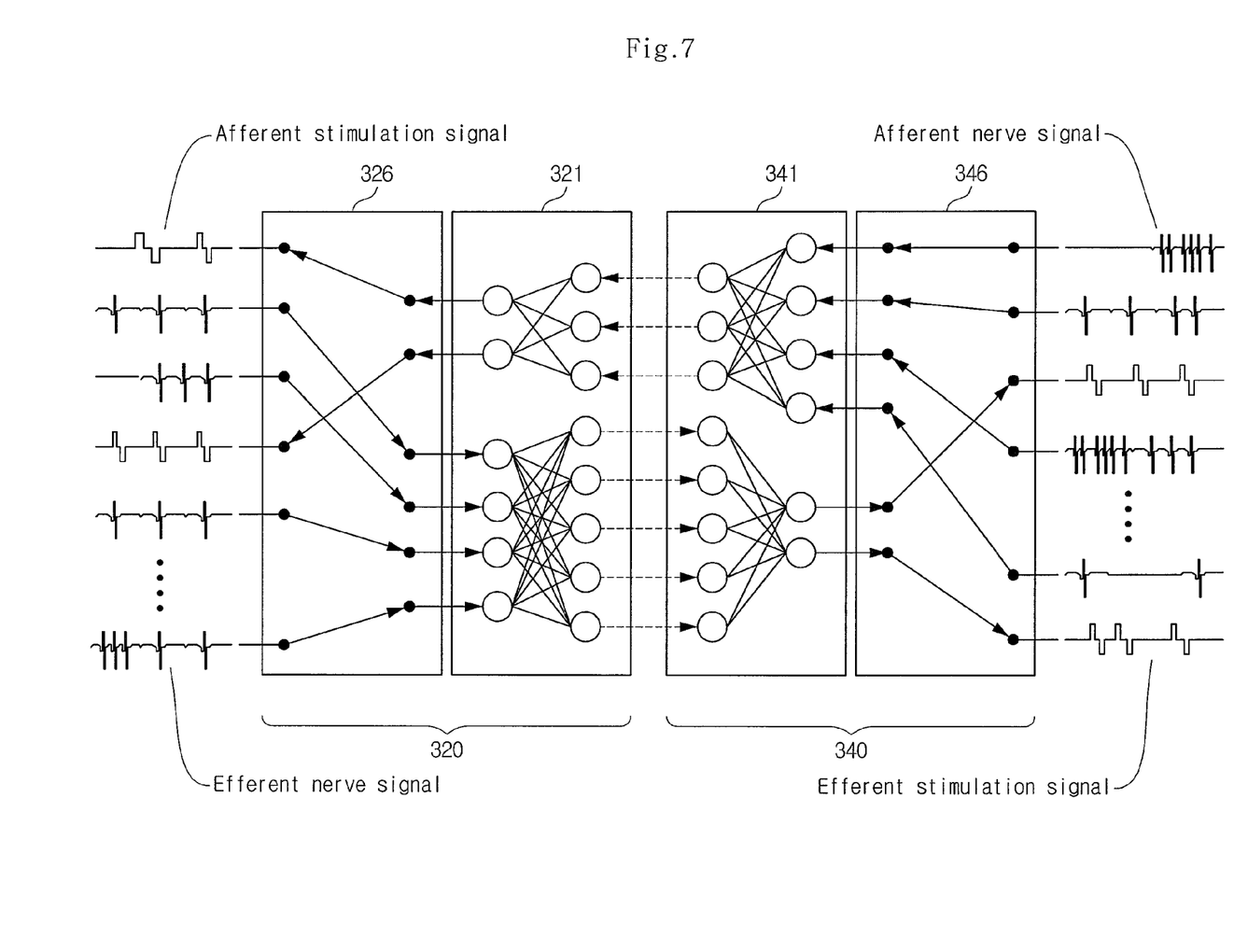
FIG. 7 illustrates a multilayer perceptron algorithm employed in an artificial nerve networking system according to an embodiment of the present disclosure.

FIG. 7 illustrates the multilayer perceptron algorithm employed in an artificial nerve networking system according to an embodiment of the present disclosure.

The artificial nerve networking algorithm of the present disclosure is executed by the digital signal processors 321, 341 of the two implantable modules 320, 340 so as to allow data transmission via wireless communication. That is to say, the efferent nerve signal from the regenerated nerve at the proximal spinal cord stump is detected and analyzed to generate an appropriate electrical stimulation pattern, and the afferent nerve signal from the regenerated nerve at the distal spinal cord stump is detected and analyzed to generate an appropriate electrical stimulation pattern. Then, the afferent nerve stimulation pulse signal is applied to the regenerated nerve at the proximal spinal cord stump.

As described above, the regenerated nerve is divided into the efferent axon 12 and the afferent axon 22. Accordingly, in order to establish the artificial nerve network, a path through which the efferent nerve signal and the afferent nerve signal can be propagated should be set up first by connecting an amplifier or electrical stimulator to the electrode depending on the axon type. As shown in FIG. 7, this process is performed by the multiplexers 326, 346 according to the command from the digital signal processors 321, 341.

As described earlier, the external controller 362 of the external module 360 monitors the afferent nerve signal resulting from physical stimulation or the efferent nerve signal resulting from intention of action, determines the type of the related axon, and sets the corresponding electrode as input or output of the artificial nerve networking algorithm.

The artificial nerve networking algorithm may be the multilayer perceptron algorithm. The multilayer perceptron architecture consists of multiple layers having opposite input/output directions depending on the flow of the nerve signal. The implantable modules 320, 340 share a hidden layer of the multilayer perceptron, and transmit data via wireless communication.

A bipolar sigmoid function is used as the activation function, and the number of neurons in the input layer, output layer and hidden layer is optimized through a learning process. During the learning process, the weight vectors of the multilayer perceptron are varied based on the data acquired from the sensory and motor rehabilitation training and from the backpropagation learning. At this time, reward for the induction of desired sensation and motion and penalty for the induction of undesired sensation and motion are defined to generate quantitated teaching values. Once the learning is completed, a stimulation pattern for inducing desired sensation and motion depending on the afferent or efferent nerve signal input to the multilayer perceptron can be obtained.

The system and method for artificial nerve networking according to the present disclosure can overcome the limitation of the existing spinal nerve treatment and provide effective functional recovery for patients with damaged nerves.

The system and method for artificial nerve networking according to the present disclosure can effectively restore the function of a damaged nerve by allowing transmission of nerve signals to and from the damaged nerve using the nerve conduit comprising the porous polymer electrode and the artificial nerve networking unit, without the need of direct connection to the regenerated nerve.

Especially, the present disclosure allows selective detection and transmission of various nerve signals and thus overcomes the limitation of the existing spinal nerve treatment.

While the present disclosure has been described with respect to the specific embodiments, it will be apparent to those skilled in the art that various changes and modifications may be made without departing from the spirit and scope of the disclosure as defined in the following claims.

What is claimed is:

1. An artificial nerve networking system comprising:
   a first nerve conduit configured for connecting at one end of a cut nerve;
   a second nerve conduit configured for connecting at the other end of the cut nerve; and
   a means for recovering the function of the cut nerve electrically connected to the first nerve conduit and the second nerve conduit and recovering the function of the cut nerve by transmitting and receiving a signal to and from the cut nerve,
   wherein the signal is transmitted and received between the one end and the other end of the cut nerve through the means for recovering the function of the cut nerve,
   wherein the first nerve conduit and the second nerve conduit each comprise:
      a support configured for connecting at an end of the cut nerve, the support having a body containing a cavity-type channel with an inner wall;
      an electrode layer formed along the inner wall of the channel; and
      an external electrode electrically connected to the electrode layer,
      wherein the channel is configured in order that nerve cells grow along the channel at the end of the cut nerve, and the electrode layer is electrically connected to the grown nerve cells,
   wherein the means for recovering the function of the cut nerve comprises:
      a first implantable module configured to be implanted in an organism and electrically connected to the first nerve conduit;
      a second implantable module configured to be implanted in the organism and electrically connected to the second nerve conduit; and
      an external module provided outside the organism,
      wherein a nerve signal is transmitted among the first implantable module, the second implantable module and the external module via wireless communication
   wherein the first implantable module and the second implantable module each comprise:
      a digital signal processor that employs a multilayer perceptron algorithm, wherein the digital signal processor receives, analyzes, and transmits a signal from one of the cut nerve, the first implantable module, the second implantable module, and the external module via wireless communication.

2. The artificial nerve networking system according to claim 1, wherein the support has a plurality of channels.

3. The artificial nerve networking system according to claim 1, wherein the first implantable module and the second implantable module each comprise:
   an amplifier amplifying the signal from the cut nerve received through the first nerve conduit and the second nerve conduit;
   an analog-to-digital (AD) converter converting the signal amplified by the amplifier to a digital signal;
   the digital signal processor receiving and analyzing the digital signal converted by the AD converter and transmitting the digital signal to one of the first implantable module, the second implantable module and the external module via wireless communication, or receiving and analyzing a digital signal received from one of the first implantable module, the second implantable module and the external module and transmitting it to the nerve cells grown along the channel;
   a digital-to-analog (DA) converter converting the digital signal received from the digital signal processor into an analog signal;
   a stimulator transmitting an electrical stimulation signal to the nerve cells grown along the plurality of channels using the analog signal converted by the DA converter; and
   a multiplexer electrically matching the nerve cells grown along the plurality of channels with the amplifier and the stimulator according to the command from the digital signal processor.

4. The artificial nerve networking system according to claim 3, wherein the first implantable module and the second implantable module each further comprise:
   an internal communication means for transmitting and receiving a signal to and from the external module via wireless communication; and
   a power receiver wirelessly receiving power from the external module.

5. The artificial nerve networking system according to claim 4, wherein the external module comprises:
   an external communication means for transmitting and receiving a signal to and from the internal communication means;
   a power supply wirelessly supplying power to the power receiver; and
   an external controller analyzing the nerve signal received from the external communication means and determining a parameter of the multilayer perceptron algorithm according to the analysis result.

* * * * *

UNITED STATES PATENT AND TRADEMARK OFFICE
CERTIFICATE OF CORRECTION

PATENT NO. : 8,666,499 B2  
APPLICATION NO. : 13/166250  
DATED : March 4, 2014  
INVENTOR(S) : In Chan Youn et al.

Page 1 of 1

It is certified that error appears in the above-identified patent and that said Letters Patent is hereby corrected as shown below:

On the Title Page, Item (75) Inventors: please change "Jun Kyo Suh" to "Jun-Kyo Francis Suh"

On the Title Page, Item (73) Assignee: please change "Korean Institute of Science and Technology" to "Korea Institute of Science and Technology"

Signed and Sealed this  
Thirteenth Day of May, 2014

Michelle K. Lee  
*Deputy Director of the United States Patent and Trademark Office*